(12) United States Patent
Tyler et al.

(10) Patent No.: US 11,446,483 B2
(45) Date of Patent: *Sep. 20, 2022

(54) PATTERNED STIMULATION INTENSITY FOR NEURAL STIMULATION

(71) Applicant: Case Western Reserve University, Cleveland, OH (US)

(72) Inventors: Dustin Tyler, Highland Heights, OH (US); Daniel Tan, Cleveland, OH (US); Matthew Schiefer, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 93 days.

This patent is subject to a terminal disclaimer.

(21) Appl. No.: 16/918,134

(22) Filed: Jul. 1, 2020

(65) Prior Publication Data

US 2020/0330751 A1 Oct. 22, 2020

Related U.S. Application Data

(63) Continuation of application No. 16/175,967, filed on Oct. 31, 2018, now Pat. No. 10,758,728, which is a (Continued)

(51) Int. Cl.
*A61N 1/36* (2006.01)
*A61N 1/05* (2006.01)

(52) U.S. Cl.
CPC ........... *A61N 1/0551* (2013.01); *A61N 1/361* (2013.01); *A61N 1/36003* (2013.01);
(Continued)

(58) Field of Classification Search
CPC ........ A61N 1/36; A61N 1/05; A61N 1/36031; A61N 1/36034; A61N 1/36178;
(Continued)

(56) References Cited

U.S. PATENT DOCUMENTS 5,397,338 A 3/1995 Grey et al.
7,647,115 B2 1/2010 Levin et al.
(Continued)

FOREIGN PATENT DOCUMENTS

CA 2825550 A1 9/2012
JP 2003503166 A 1/2003
(Continued)

OTHER PUBLICATIONS

Japanese Office Action for corresponding Japanese Application Serial No. 2020-088237, dated Apr. 20, 2021, pp. 1-7.
(Continued)

*Primary Examiner* — Jon Eric C Morales
(74) *Attorney, Agent, or Firm* — Tarolli, Sundheim, Covell & Tummino LLP

(57) ABSTRACT

One aspect of the present disclosure relates to a system that can modulate the intensity of a neural stimulation signal over time. A pulse generator can be configured to generate a stimulation signal for application to neural tissue of an individual and modulate a parameter related to intensity of a pattern of pulses of the stimulation signal over time. An electrode can be coupled to the pulse generator and configured to apply the stimulation signal to the neural tissue. A population of axons in the neural tissue can be recruited with each pulse of the stimulation signal.

18 Claims, 7 Drawing Sheets

Related U.S. Application Data continuation of application No. 15/104,589, filed as application No. PCT/US2014/070435 on Dec. 16, 2014, now Pat. No. 10,960,203, which is a continuation of application No. PCT/US2013/075329, filed on Dec. 16, 2013.

(52) U.S. Cl.
CPC ....... *A61N 1/36014* (2013.01); *A61N 1/3615* (2013.01); *A61N 1/36031* (2017.08); *A61N 1/36034* (2017.08); *A61N 1/36067* (2013.01); *A61N 1/36103* (2013.01); *A61N 1/36139* (2013.01); *A61N 1/36146* (2013.01); *A61N 1/36178* (2013.01); *A61N 1/36189* (2013.01)

(58) Field of Classification Search
CPC ............ A61N 1/36003; A61N 1/36139; A61N 1/36146; A61N 1/36067; A61N 1/36014; A61N 1/3615; A61N 1/36103; A61N 1/0551; A61N 1/36189; A61N 1/361
See application file for complete search history.

(56) References Cited

U.S. PATENT DOCUMENTS

| | | | |
|---|---|---|---|
| 8,165,695 | B2 | 4/2012 | Diubaldi et al. |
| 9,421,366 | B2 | 8/2016 | Tyler et al. |
| 10,758,728 | B2 * | 9/2020 | Tyler ............... A61N 1/36014 |
| 2004/0267333 | A1 | 12/2004 | Krongberg |
| 2009/0093856 | A1 | 4/2009 | Attila et al. |
| 2011/0230931 | A1 | 9/2011 | Hagege |
| 2012/0197356 | A1 | 8/2012 | Wei et al. |
| 2012/0303080 | A1 | 11/2012 | Ben-Davud et al. |
| 2014/0180361 | A1 | 6/2014 | Burdick et al. |
| 2014/0257428 | A1 | 9/2014 | Zhu |
| 2014/0304773 | A1 | 10/2014 | Woods et al. |
| 2015/0328465 | A1 | 11/2015 | Tyler et al. |
| 2016/0121124 | A1 | 5/2016 | Johanek et al. |
| 2019/0346925 | A1 | 11/2019 | Daniels |

FOREIGN PATENT DOCUMENTS

| | | |
|---|---|---|
| JP | 2006239447 A | 9/2006 |
| JP | 2013503166 | 8/2009 |
| JP | 2013523410 | 4/2010 |
| JP | 2010162191 A | 7/2010 |
| JP | 2010540088 A | 12/2010 |
| JP | 2013503166 | 1/2013 |
| JP | 2013523410 | 6/2013 |
| WO | 2001/02054 A2 | 1/2001 |
| WO | 2011/130488 A2 | 10/2011 |
| WO | 2011/136912 A1 | 11/2011 |
| WO | 2012/129574 | 9/2012 |
| WO | 2012129574 | 9/2012 |
| WO | 2014/093964 | 6/2014 |
| WO | 2014093964 | 6/2014 |
| WO | WO2014/093964 | 6/2014 |
| WO | 2015/095092 | 6/2015 |
| WO | WO2015/095092 | 6/2015 |

OTHER PUBLICATIONS

Australian Examination Report No. 1 for corresponding Australian Application Serial No. 2018220123, dated Apr. 23, 2019, pp. 1-3.
Canadian Office Action corresponding to Canadian Patent Application No. 2,933,555, dated Mar. 15, 2018, pp. 1-5.
Canadian Office Action corresponding to Canadian Patent Application No. 2905042, dated Jul. 13, 2017, pp. 1-3.
Canadian Office Action corresponding to Canadian Patent Application No. 2933555, dated Apr. 21, 2017, pp. 1-3.
Canadian Office Action for corresponding Canadian Application Serial No. 2,933,555, dated Mar. 15, 2018, pp. 1-5.
Canadian Office Action for corresponding Canadian Application Serial No. 2905042, dated Jan. 13, 2017, pp. 1-3.
Canadian Office Action for corresponding Canadian Application Serial No. 2933555, dated Apr. 21, 2017, pp. 1-3.
European Office Action corresponding to European Application No. 13818098.9, 3 pages, dated Jan. 30, 2017.
European Office Action corresponding to European Application No. 14827322.0, dated Jul. 25, 2017, pp. 1-2.
European Office Action for corresponding European Application Serial No. 13818098.9, dated Jan. 30, 2017, pp. 1-3.
European Office Action for corresponding European Application Serial No. 14827322.0, dated Jul. 25, 2017, pp. 1-2.
Japanese Office Action corresponding to Japanese Patent Application No. 2015-548039, dated May 30, 2017, pp. 1-3.
Japanese Office Action corresponding to Japanese Patent Application No. 2016-540048, dated Jul. 4, 2017, pp. 1-4.
Japanese Office Action for corresponding Japanese Application Serial No. 2015-548039, dated May 30, 2017, pp. 1-3.
Japanese Office Action for corresponding Japanese Application Serial No. 2016-540048, dated Jul. 4, 2017, pp. 1-4.
Japanese Office Action for corresponding Japanese Application Serial No. 2018-061564, dated Mar. 12, 2019, pp. 1-7.
Japanese Office Action for the corresponding Japanese Application Serial No. 2019-040222, dated Mar. 24, 2020, pp. 1-5.
Patent Examination Report No. 1 for Application No. 2014366175, dated Oct. 17, 2016, pp. 1-4.
Patent Examination Report No. 1 for corresponding Application Serial No. 2014366175, dated Oct. 17, 2016, pp. 1-4.
PCT International Search Report for corresponding International Application Serial No. PCT/US2014/070435, dated Apr. 2, 2015, pp. 1-6.
PCT International Search Report for PCT/US2014/070435 dated Apr. 2, 2015, pp. 1-6.
Extended European Search Report for corresponding European Application Serial No. 21188273.3, dated Oct. 6, 2021, pp. 1-7.
Canadian Office Action for corresponding Canadian Application Serial No. 2,983,500, dated Jul. 20, 2020, pp. 1-6.
Canadian Office Action for corresponding Canadian Application Serial No. 2,998,221, dated Jul. 27, 2021, pp. 1-4.
European Office Action for corresponding European Application Serial No. 13818098.9, dated Mar. 23, 2022, pp. 1-5.

* cited by examiner

PATTERNED STIMULATION INTENSITY FOR NEURAL STIMULATION

This application is a Continuation of U.S. patent application Ser. No. 16/175,967, filed Oct. 31, 2018, which is a Continuation of U.S. patent application Ser. No. 15/104,589, filed Jun. 15, 2016, which is a U.S. National Stage under 35 USC 371 patent application claiming priority to Serial No. PCT/US2014/070435, filed on Dec. 16, 2014, which is a Continuation of Patent Application Serial No. PCT/US2013/075329, filed Dec. 16, 2013. Each of which is hereby incorporated by reference for all purposes.

TECHNICAL FIELD

The present disclosure relates generally to neural stimulation and, more specifically, to systems and methods that can modulate the intensity of a pattern of pulses in a neural stimulation signal.

BACKGROUND

Through neural stimulation, an electrical signal can activate or suppress a part of an individual nervous system to replace and/or augment a biological function of the individual (e.g., a motor function, a sensory function, an autonomic function, an organ function, and/or a cognitive function). Traditionally, the electrical signal has included trains of identical electric pulses (e.g., constant frequency, amplitude, and interpulse interval), each providing a regular intensity stimulation. However, these trains of identical electric pulses often do not mimic normal biological functions. For example, when responding to a sensory input, normal afferent neurons can generate non-constant patterns of action potentials synchronously on a population of axons. When a regular train of identical pulses is applied to these afferent neurons, a corresponding regular train of synchronous action potentials can be transmitted to the brain. The regular train of action potentials can be interpreted by the brain as foreign, resulting in a tingling sensation or other abnormal sensory perception.

SUMMARY

The present disclosure relates generally to neural stimulation and, more specifically, to systems and methods that can modulate the intensity (e.g., strength and/or timing) of a pattern of pulses in a neural stimulation signal. For example, the neural stimulation signal can include a train of pulses, and a parameter associated with the intensity of a pattern of these pulses can be modified over time. The neural stimulation signal with such patterned stimulation intensity (or "Ψ-stim") can mimic normal neurological functions, allowing the neural stimulation signal to affect different biological functions, including sensory functions (e.g., perception), autonomic functions, motor functions, and/or cognitive function.

In one aspect, the present disclosure can include a system that can modulate the intensity (e.g., strength and/or timing) of a neural stimulation signal over time. A pulse generator can be configured to generate a stimulation signal for application to neural tissue of an individual and modulate a parameter related to intensity of a pattern of pulses of the stimulation signal over time. An electrode can be coupled to the pulse generator and configured to apply the stimulation signal to the neural tissue. For example, the modulation of the intensity over time can lead to different populations of axons in the neural tissue to be recruited based on the modulation of the intensity.

In another aspect, the present disclosure can include a method for neural stimulation signal. A parameter related to an intensity (e.g., strength and/or timing) of a pulse of the stimulation signal is modulated with time. Different populations of axons in the neural tissue can be recruited with each pulse of the stimulation signal. A desired bodily function can be affected in the individual based on the stimulation signal. In some instances, the method can involve identifying an individual in need of neural stimulation and applying the neural stimulation signal to the individual in need of the neural stimulation. For example, in the instance of a diseased individual, the method can include identifying the individual suffering from the diseased condition.

In a further aspect, the present disclosure can include a device that can modulate the intensity (e.g., strength and/or timing) of a neural stimulation signal over time. A pulse generator can be configured to a feedback signal based on the neural stimulation signal. For example, the feedback signal can be a physiological signal, a sensor signal, an input signal, or the like. The pulse generator can be further configured to modulate a parameter related to intensity of a pattern of pulses of the stimulation signal based on the feedback signal.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
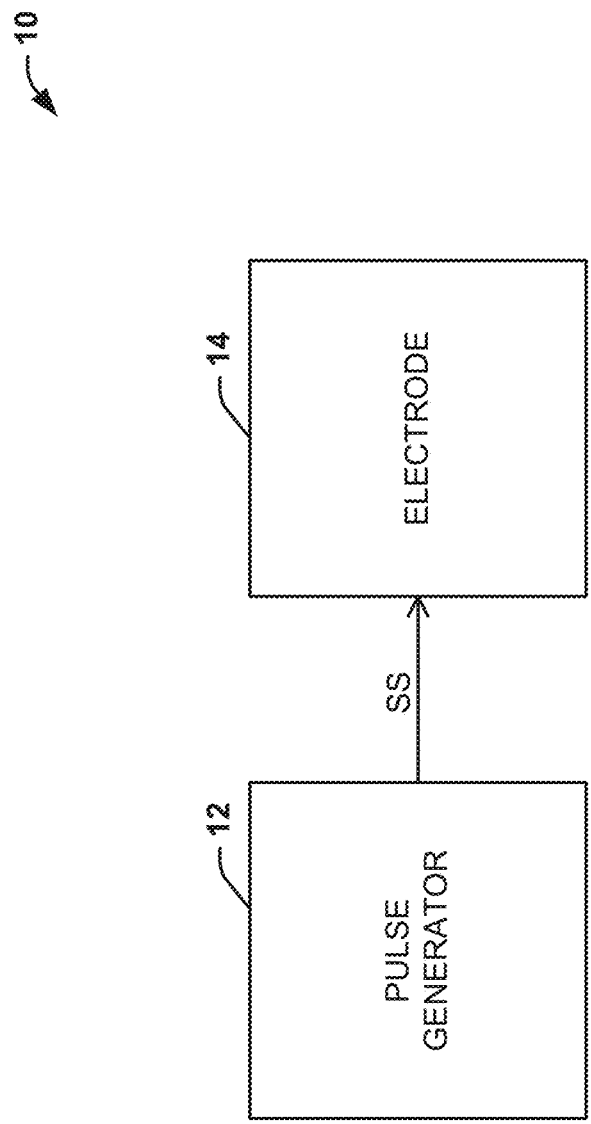
FIG. 1 is a block diagram showing a system that can modulate the intensity of a neural stimulation signal in accordance with an aspect of the present disclosure.

In the context of the present disclosure, the singular forms "a," "an" and "the" can also include the plural forms, unless the context clearly indicates otherwise. The terms "comprises" and/or "comprising," as used herein, can specify the presence of stated features, steps, operations, elements, and/or components, but do not preclude the presence or addition of one or more other features, steps, operations, elements, components, and/or groups. As used herein, the term "and/or" can include any and all combinations of one or more of the associated listed items. Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "neural stimulation" can refer to the therapeutic activation or suppression of at least a portion of an individual nervous system to replace, restore, and/or augment a biological function via a stimulation signal. In some instances, the stimulation signal can be applied to the individual's neural tissue through one or more electrodes.

As used herein, the term "stimulation signal" can refer to a signal that can activate or suppress a portion of an individual's nervous system to replace, restore, and/or augment a biological function of the individual. For example, the stimulation signal can include one or more of an electrical signal, a magnetic signal, an optical signal, an optogenetic signal, a chemical signal, or the like. In some instances, the stimulation signal can include a train of pulses.

As used herein, the term "pulse" can refer to a non-sinusoidal waveform of current and/or voltage. In some instances, a pulse can be charge-balanced. In other instances, a plurality of pulses can be arranged in one or more patterns of pulses. Example shapes of a pulse can include square, rectangular, ramp, logarithmic, exponential, and the like.

As used herein, the term "biological function" can refer to a process that takes place within an individual's body controlled by the nervous system. Examples of biological functions can include motor functions, sensory functions, autonomic functions, organ functions, and cognitive functions. The terms "biological function" and "bodily function" can be used interchangeably herein.

As used herein, the term "electrode" can refer to one or more electrical conductors that contact(s) a portion of an individual's body to deliver a stimulation signal. In some instances, each individual electrical conductor can be referred to as a "contact". For example, an electrode can be a multi-contact electrode and/or a plurality of single-contact electrodes.

As used herein, the term "neural tissue" can refer to a population of axons that can react to stimuli and conduct impulses to various organs or tissues in the body that bring about a response to the stimuli. The neural tissue can include, for example, populations of central nervous system axons (e.g., axons within the brain and/or the spinal cord) or populations of peripheral nervous system axons (e.g., motor axons, autonomic axons, and/or sensory axons). The terms "axon" and "neural fiber" can be used interchangeably herein.

As used herein, the term "patterned stimulation intensity" (or "Ψ-stim") can refer to a variation of one or more stimulation parameter related to the intensity of a pattern of pulses in a neural stimulation signal. In one example, "patterned intensity stimulation" can refer to population-based encoding of neural tissue because the variation of the one or more stimulation parameters can lead to recruitment of different populations of axons within the neural tissue. The terms "pattern intensity modulation" and "patterned stimulation intensity" can be used interchangeably herein.

As used herein, the term "intensity" of the stimulation signal can refer to the strength and/or timing of the stimulation signal. In some instances, the intensity can correspond to the number of neural fibers that are recruited by a pulse and/or pattern of pulses of a stimulation signal.

As used herein, the term "stimulation parameter" can refer to a parameter of a pulse and/or pattern of pulses associated with the intensity of a stimulation signal. Examples of stimulation parameters can include amplitude, pulse width, interpulse interval, pulse shape (e.g., square, rectangular, exponential, logarithmic, ramp, etc.), parameters affecting pulse shape, recharge phase amplitude, recharge delay, and the like. The terms "stimulation parameters," "intensity parameters," and "pulse parameters" can be used interchangeably herein.

As used herein, the term "individual" can refer to any warm-blooded organism including, but not limited to, a human being, a pig, a rat, a mouse, a dog, a cat, a goat, a sheep, a horse, a monkey, an ape, a rabbit, a cow, etc. The terms "individual," "subject," "patient," and "user" can be used interchangeably herein unless otherwise indicated.

II. Overview

The present disclosure relates generally to neural stimulation and, more specifically, to systems and methods that can modulate the intensity (e.g., strength and/or timing) of a pattern of pulses in a neural stimulation signal. For example, a stimulation signal for application to neural tissue of an individual can be generated and a parameter related to intensity of a pattern of pulses of the stimulation signal can be modulated over time. When the stimulation signal is applied to the neural tissue, a population of axons in the neural tissue can be recruited with each pulse of the stimulation signal.

The neural stimulation with patterned stimulation intensity (or "Ψ-stim") in the peripheral nervous system and/or the central nervous system can affect different biological functions, including sensory functions (e.g., perception), autonomic functions, motor functions, organ functions, and/or cognitive functions. For example, the neural stimulation can be used to affect a biological function in a normal able-bodied individual; an amputee; a paralyzed individual; or a diseased individual, such as an individual suffering from an autonomic, motor, and/or sensory deficit. In one example, the biological function can include sensory restoration in amputees or paralyzed individuals. The sensory restoration can include providing a "virtual" sensation to replace the missing biological sensation. In another example, the biological function can include providing an artificial sensation to an able-bodied individual by stimulating the median, ulnar and/or radial nerves for touch-enabled virtual reality, user interfaces, clinical diagnoses, mechanical diagnoses, robotic control, and/or telepresence.

Other examples of the biological function can include modulation of pain, such as, for example, modulating the individual's perception of pain. In a further example, the biological function can include restoration or augmentation of taste, smell, hearing, vision or touch. In yet another example, the biological function can include regulation of swallowing. In still another example, the biological function can include regulation of gastric reflux. In yet another example, the biological function can include regulation of blood pressure, appetite, or the like. In yet another example, the biological function can include restoration of sexual sensation or enhancement of sexual sensation. In a further example, the biological function can include genito-urinary regulation, such as relieving incontinence, regulating voiding, other bladder functions, and the like. In another example, the biological function can include improving lactation for breastfeeding. In another example, the biological function is restoring sensory perception of removed or missing tissue in an individual. In yet another example, sensory perception of removed breast tissue can be restored in an individual who has undergone a mastectomy. In still another example, the biological function can include regulation of a movement disorder. For the different biological functions, electrodes can be placed in different areas of the individual's body and the patterned intensity modulation of the stimulation signal can lead to recruitment of different populations of axons within the neural tissue.

III. Systems

One aspect of the present disclosure can include a system that can modulate the intensity of a neural stimulation signal. Although not wishing to be bound by theory, it is believed that by modulating the intensity of the neural stimulation signal, the neural stimulation signal can mimic normal neurological functions of an individual more closely than traditional stimulation with a regular train of identical pulses. When the stimulation signal is applied to the neural tissue, the modulation can allow different populations of axons in the neural tissue to be recruited with each pulse of the stimulation signal.

FIG. 1 illustrates an example of a system 10 that can modulate the intensity (e.g., strength and/or timing) of a neural stimulation signal, according to an aspect of the present disclosure. The system 10 can include a pulse generator 12 to generate and modulate a stimulation signal (SS) and an electrode 14 to apply the stimulation signal (SS) to an individual's neural tissue. The stimulation signal (SS), in some examples, can be a time-varying electrical signal. In some examples, the pulse generator 12 can employ patterned stimulation intensity (or "Ψ-stim") to vary one or more parameters related to intensity of the stimulation signal (SS). As noted, the neural stimulation with patterned stimulation intensity can activate and/or suppress different biological functions, including sensory functions (e.g., perception), autonomic functions, motor functions, organ functions, and/or cognitive functions, of a normal individual, an amputee, a paralyzed individual, a diseased individual, or the like.

The pulse generator 12 can be a device configured to generate the stimulation signal (SS). In some instances, the pulse generator 12 also can be configured to modulate a parameter related to intensity of a pattern of pulses of the stimulation signal. As an example, the pulse generator 12 can modulate the parameter related to the intensity over time. In another example, the pulse generator 12 can generate and/or modulate the stimulation signal (SS) based on based on a desired bodily function. As another example, shown in FIG. 2, the pulse generator 12 can be configured to generate and/or modulate the stimulation signal (SS) based on an input related to the desired bodily function.

Figure 2:
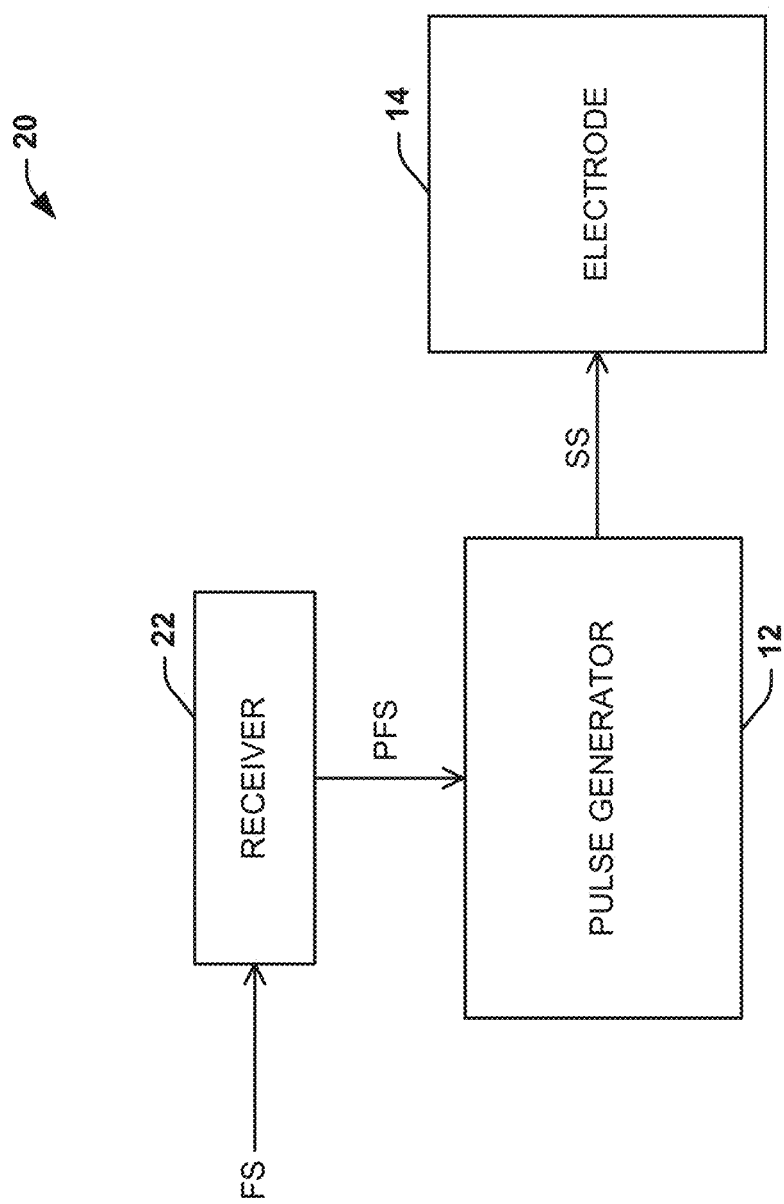
FIG. 2 is a block diagram showing a receiver that can be part of the system of FIG. 1 to receive a feedback signal that can be utilized in the modulation of the intensity of the neural stimulation signal.

In the example shown in FIG. 2, the pulse generator 12 can be coupled to a receiver 22. In some instances, the pulse generator 12 and the receiver 22 can be embodied as components of a single device. In other instances, the pulse generator 12 and the receiver 22 can each be embodied as separate devices coupled together via a wired and/or wireless connection that facilitates communication between the pulse generator 12 and the receiver 22.

One or more functions of pulse generator 12 and/or the receiver 22 can be implemented by computer program instructions. These computer program instructions can be provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the pulse generator 12 and/or the receiver 22.

These computer program instructions can also be stored in a non-transitory computer-readable memory that can direct a computer or other programmable data processing apparatus to function in a particular manner, such that the instructions stored in the non-transitory computer-readable memory produce an article of manufacture including instructions, which implement the functions of the pulse generator 12 and/or the receiver 22.

The computer program instructions can also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions of the components specified in the block diagrams and the associated description.

Accordingly, the pulse generator 12 and/or the receiver 22 can be embodied at least in part in hardware and/or in software (including firmware, resident software, microcode, etc.). Furthermore, aspects of the system 10 can take the form of a computer program product on a computer-usable or computer-readable storage medium having computer-usable or computer-readable program code embodied in the medium for use by or in connection with an instruction execution system. A computer-usable or computer-readable medium can be any non-transitory medium that is not a transitory signal and can contain or store the program for use by or in connection with the instruction or execution of a system, apparatus, or device. The computer-usable or computer-readable medium can be, for example but not limited to, an electronic, magnetic, optical, electromagnetic, infrared, or semiconductor system, apparatus or device. More specific examples (a non-exhaustive list) of the computer-readable medium can include the following: a portable computer diskette; a random access memory; a read-only memory; an erasable programmable read-only memory (or Flash memory); and a portable compact disc read-only memory.

Such functions of the receiver 22 can include receiving an input signal (FS) and transmitting data related to the input signal (PFS) to the pulse generator 12. In some instances, the receiver 22 can be configured to perform signal processing on the input signal (FS). For example, the signal processing employed by the receiver 22 can transform the input signal (FS) into data related to the input signal (PFS). The data related to the input signal (PFS) can be transmitted to the pulse generator 12.

The pulse generator 12 can be configured to generate and/or modulate the stimulation signal (SS) based on the data related to the input signal (FS). For example, the input signal (FS) can include a user input, a feedback signal input from the neural tissue or other tissue, a sensor signal input, a time input, etc. As another example, the input signal can include an input related to a stimulation paradigm defining a modulation pattern or envelope that can be employed by the pulse generator 12.

In either system 10 of FIG. 1 or system 20 of FIG. 2, the stimulation signal (SS) generated by the pulse generator 12 can include a plurality of pulses. In some instances, the plurality of pulses can be charge-balanced (cathodic first and/or anodic first). In other instances, a pattern of the plurality of pulses can be charge-balanced, even if the individual pulses are not charge-balanced. In still other instances, the plurality of pulses need not be charge-balanced, but can be employed over a time period that is sufficiently short so that any electrochemical reactions products generated are not generated in a quantity large enough to cause damage to surrounding tissue or the electrode 14.

The pulse generator 12 can modulate the stimulation signal (SS) by modulating one or more pulse parameters related to intensity of the stimulation signal (SS). The modulation of the one or more pulse parameters of the stimulation signal (SS) related to intensity can recruit a different population of axons with each pulse. For example, the pulse generator 12 can vary the pulse parameter related to intensity for each of the pulses. As another example, the pulse generator 12 can vary the pulse parameter related to intensity for a plurality of pulses according to a stimulation paradigm that defines a modulation pattern or modulation envelope. The modulation pattern or modulation envelope can be any shape representing a time-varying alternation of one or more pulse parameters related to intensity of the stimulation signals (SS). Example shapes of the modulation pattern or modulation envelope can include a sinusoid, a triangle, a trapezoid, or the like. In some instances, a single pulse parameter related to intensity can be modulated by the pulse generator 12. In other instances, different pulse parameters related to intensity can be modulated by the pulse generator 12 at different times. In still other instances, a plurality of different pulse parameters related to intensity can be modulated by the pulse generator 12 at the same time (or substantially the same time).

The one or more stimulation parameters can be any parameter of a pulse and/or a pattern of pulses that relates to the intensity of the stimulation signal. Examples of stimulation parameters related to intensity can include amplitude, pulse width, interpulse interval, pulse shape, parameters affecting pulse shape, recharge phase amplitude, recharge delay, and the like. Other examples of intensity parameters can include a parameter related to the modulation envelope (e.g., shape, frequency, amplitude, etc.).

Figure 3:
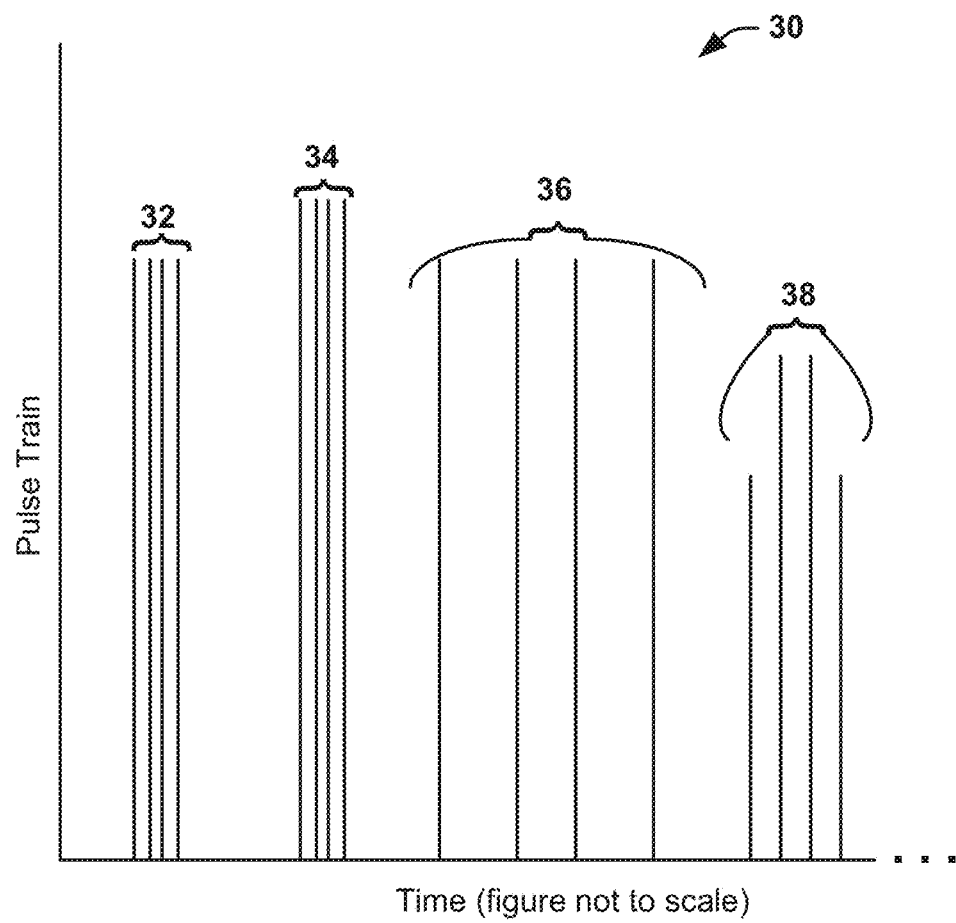
FIG. 3 is a graph showing examples of modulations of the intensity of the neural stimulation signal that can be done by the system shown in FIG. 1.

FIG. 3 shows examples of different modulations that can be done to a series of pulses by the pulse generator 12 as a graph of a feature of the pulse train (e.g., pulse intensity) over time. The graph of FIG. 3 is an exemplary schematic illustrating different parameters of a stimulation signal (SS) that can be modulated. In FIG. 3, a baseline signal is shown at 32. The amplitude of the baseline signal can be varied at 34. The interpulse interval can be varied at 36. The interpulse interval and the amplitude/shape can be varied in combination at 38. At elements 34 and 36, a single parameter is varied for the group of pulses. At 38, a parameter (interpulse interval) is varied for the group of pulses and a parameter (amplitude) is varied for individual pulses. Additional parameters can be modulated that are not illustrated in FIG. 3 (e.g., any parameter of a pulse and/or a pattern of pulses that relates to the intensity of the stimulation signal, such as pulse width, parameters affecting pulse shape, recharge phase amplitude, recharge delay, a parameter related to the modulation envelope (e.g., shape, frequency, amplitude, etc.).

Referring again to FIGS. 1 and 2, the electrode 14 can be coupled to the pulse generator 12 to receive the stimulation signal (SS) transmitted by the pulse generator. The electrode 14 can interface with the neural tissue of the individual to deliver the stimulation signal (SS) to the neural tissue to affect the desired biological function. The electrode 14 can be placed transcutaneously, subcutaneously, or directly on the neural tissue to be stimulated. In some instances, the neural tissue that the electrode 14 can interface with can include a portion of the central nervous system (e.g., for deep brain stimulation, spinal stimulation, or the like). For example, deep brain stimulation can be used to treat movement disorders, such as essential tremor or Parkinson's disease. In another example, deep brain stimulation and/or spinal cord stimulation can also be used to manage pain. In other instances, the neural tissue that the electrode can interface with can include a portion of the peripheral nervous system (e.g., a nerve (e.g., an afferent nerve, an efferent nerve, and/or an autonomic nerve) and/or ganglia).

Figure 5:
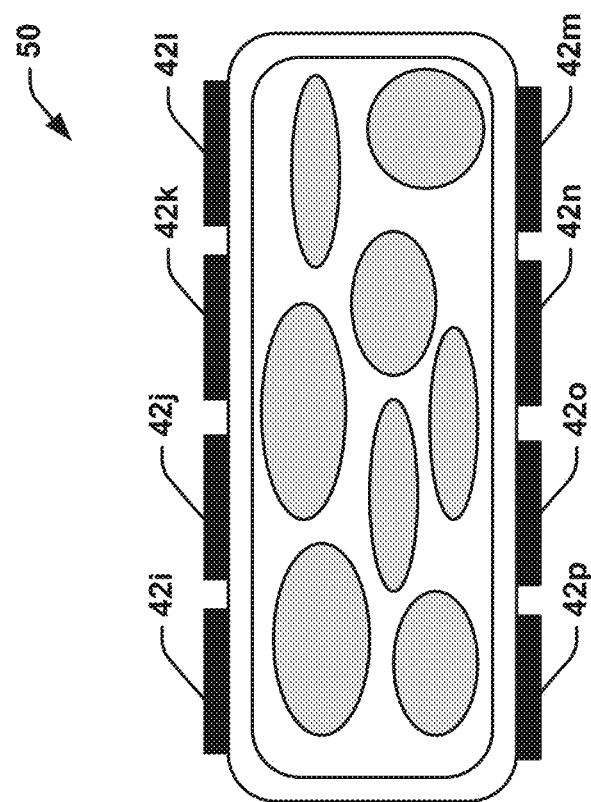
FIGS. 4 and 5 are example illustrations of electrodes that can be part of the system shown in FIG. 1.
Figure 4:
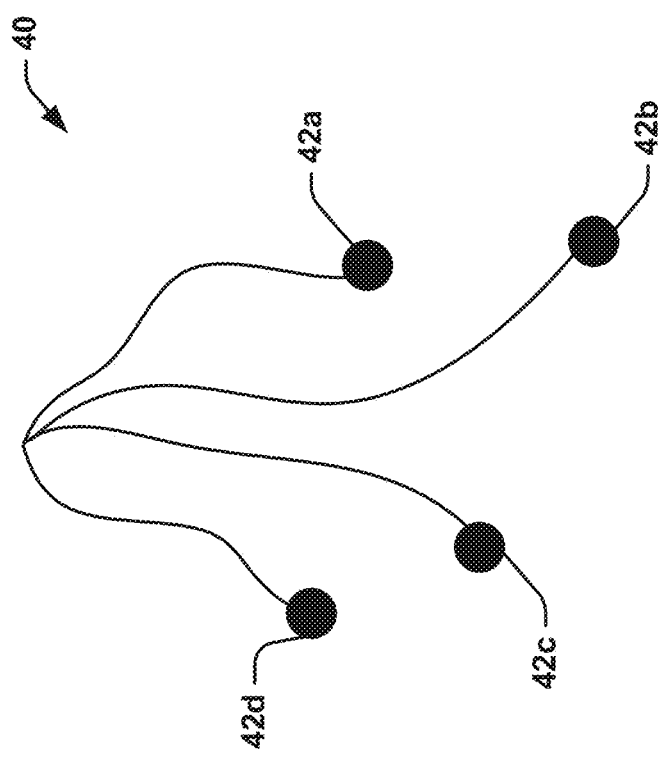

In some instances, the electrode 14 can include a set of multiple contacts that can include N electrode contacts, where N is a positive integer greater than or equal to two. For example, the pulse generator 12 can modulate the timing and the strength of each pulse in the stimulation signal (SS) between the multiple contacts to alter an electric field delivered to the neural tissue by the electrode 14. In some instances, as schematically illustrated in FIG. 4, the electrode 14 (e.g., an electrode array) can include a plurality of single-contact electrodes 42a-d. For example, the plurality of electrodes can be between or within fascicles. In another example, the electrodes can be located within the brain and/or the spinal cord. In other instances, as schematically illustrated in FIG. 5, the electrode 14 can include a multi-contact electrode (e.g., a nerve cuff electrode, a spiral electrode, etc.) with a plurality of contacts 42m-i.

As noted, the stimulation signal (SS) with patterned stimulation intensity from the pulse generator 12 can affect different biological functions, including sensory functions (e.g., perception), autonomic functions, motor functions, organ functions, and/or cognitive functions. In one example, the biological function can include sensory restoration in amputees or paralyzed individuals. In another example, the biological function can include modulation of pain. In a further example, the biological function can include restoration of taste. In yet another example, the biological function can include regulation of swallowing. In still another example, the biological function can include regulation of gastric reflux. In yet another example, the biological function can include regulation of blood pressure, appetite, or the like. In still a further example, the biological function can include restoration of hearing, vision, or the like. In yet another example, the biological function can include restoration of sexual sensation or enhancement of sexual sensation. In a further example, the biological function can include genito-urinary regulation, such as relieving incontinence, regulating voiding, and the like. In yet another example, sensory perception of removed breast tissue can be restored in an individual who has undergone a mastectomy. In still another example, the biological function can include regulation of a movement disorder. For the different biological functions, electrodes can be placed in different areas of the individual's body and the patterned intensity modulation of the stimulation signal can lead to recruitment of different populations of axons within the neural tissue.

IV. Methods

Figure 6:
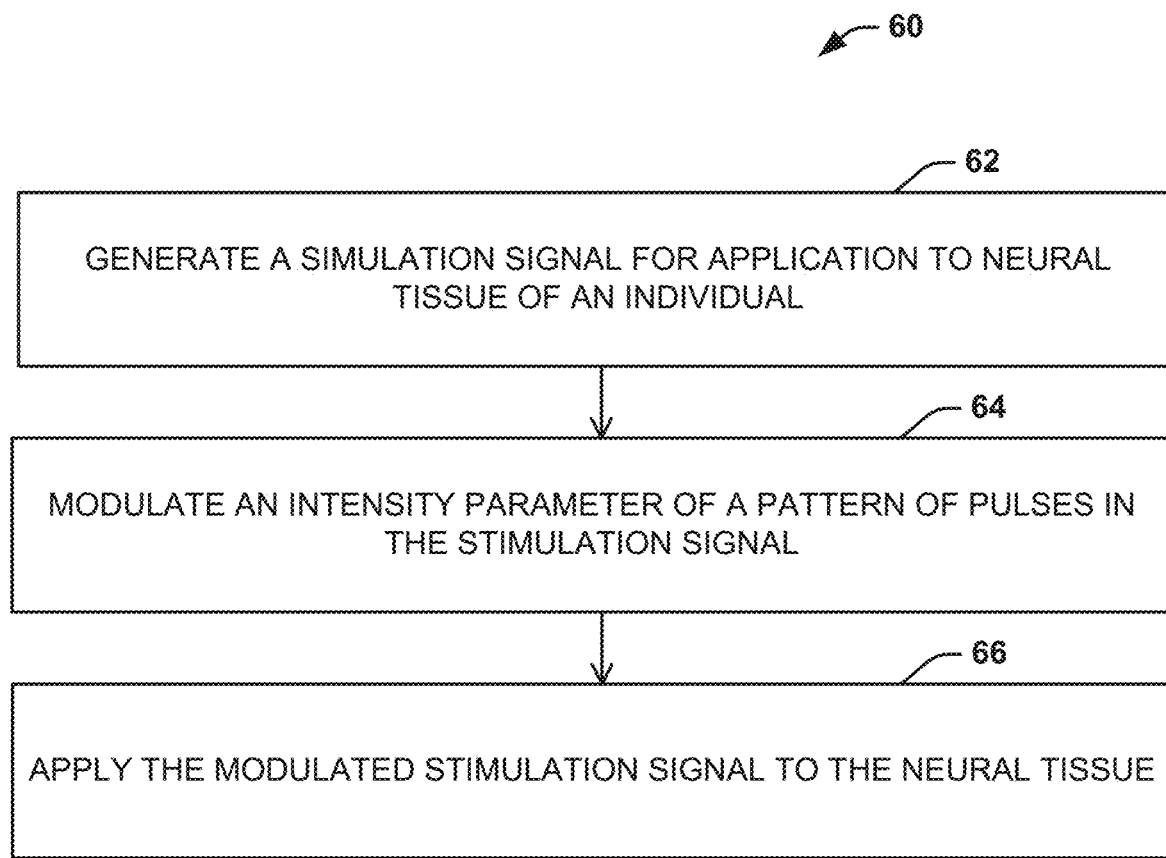
FIG. 6 is a process flow diagram illustrating a method for neural stimulation in accordance with another aspect of the present disclosure.
Figure 7:
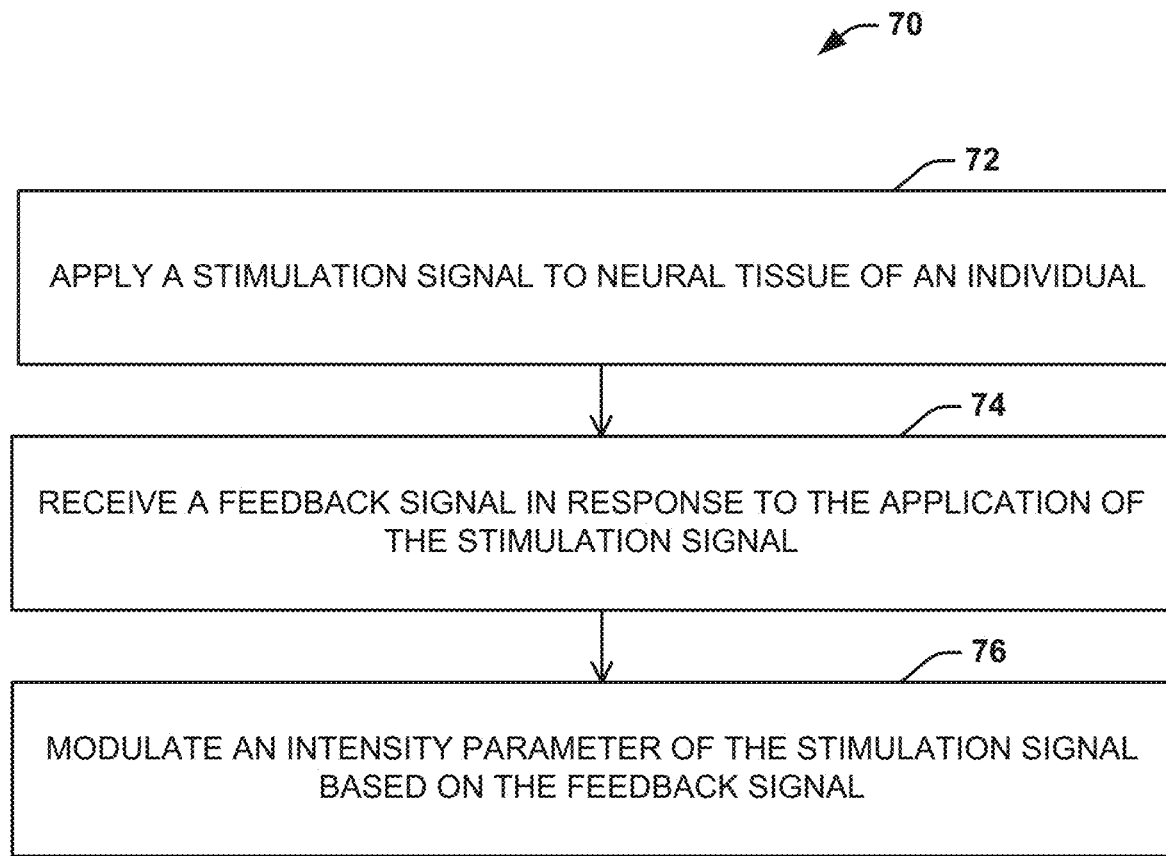
FIG. 7 is a process flow diagram illustrating a method for modulating the intensity of a signal used for the neural stimulation in the method shown in FIG. 6.
Figure 8:
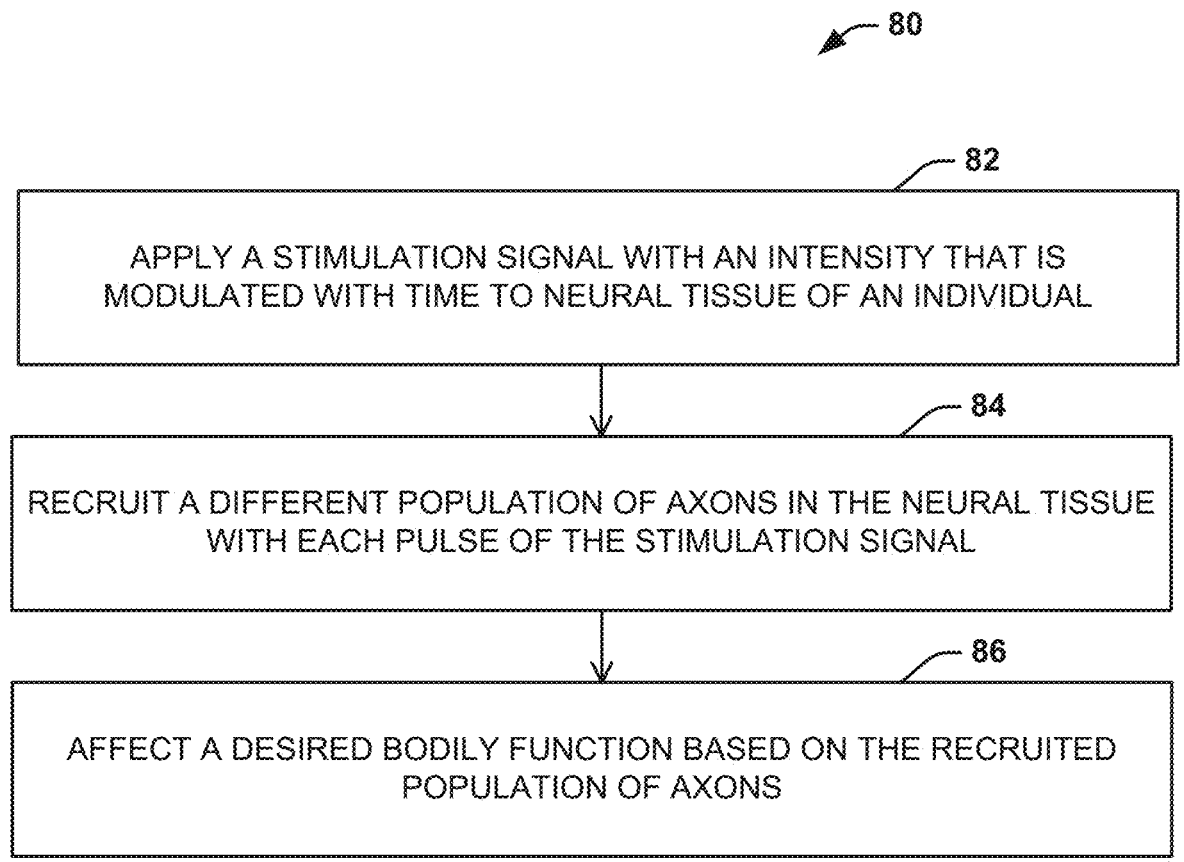
FIG. 8 is a process flow diagram illustrating a method for affecting a desired bodily function with the neural stimulation in the method shown in FIG. 6.

Another aspect of the present disclosure can include methods for modulating the intensity (e.g., strength and/or timing) of a neural stimulation signal. An example of a method 60 for neural stimulation to affect a desired bodily function is shown in FIG. 6. Another example of a method 70 for modulating the intensity of a signal used for the neural stimulation is shown in FIG. 7. A further example of a method 80 for affecting a desired bodily function with the neural stimulation is shown in FIG. 8. In some instances, the method can involve identifying an individual in need of neural stimulation and applying the neural stimulation signal to the individual in need of the neural stimulation. For example, in the instance of a diseased individual, the method can include identifying the individual suffering from the diseased condition.

The methods 60-80 of FIGS. 6-8, respectively, are illustrated as process flow diagrams with flowchart illustrations. For purposes of simplicity, the methods 60-80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 60-80.

One or more blocks of the respective flowchart illustrations, and combinations of blocks in the block flowchart illustrations, can be implemented by computer program instructions. These computer program instructions can be stored in memory and provided to a processor of a general purpose computer, special purpose computer, and/or other programmable data processing apparatus to produce a machine, such that the instructions, which execute via the processor of the computer and/or other programmable data processing apparatus, create mechanisms for implementing the steps/acts specified in the flowchart blocks and/or the associated description. In other words, the steps/acts can be implemented by a system comprising a processor that can access the computer-executable instructions that are stored in a non-transitory memory.

The methods 60-80 of the present disclosure may be embodied in hardware and/or in software (including firmware, resident software, micro-code, etc.). Furthermore, aspects of the present disclosure may take the form of a computer program product on a computer-usable or computer-readable storage medium having computer-usable or computer-readable program code embodied in the medium for use by or in connection with an instruction execution system. A computer-usable or computer-readable medium may be any non-transitory medium that can contain or store the program for use by or in connection with the instruction or execution of a system, apparatus, or device.

Referring to FIG. 6, an aspect of the present disclosure can include a method 60 for neural stimulation to affect a bodily function. At 62, a stimulation signal (e.g., SS) can be generated (e.g., by pulse generator 12) for application to neural tissue of an individual. The neural tissue can include central nervous system tissue and/or peripheral nervous system tissue (motor nerves, sensory nerves, and/or autonomic nerves). The stimulation signal can be configured with parameters tailored for the desired biological function. For example, the stimulation signal can include a plurality of pulses that can be arranged in patterns. As noted, the neural stimulation can be applied to a normal individual, an amputee, a paralyzed individual, a diseased individual, or the like. For example, the stimulation signal can include a plurality of pulses (e.g., arranged in a modulation pattern or envelope).

At 64, an intensity parameter of a pattern of pulses in the stimulation signal can be modified (e.g., by pulse generator 12). The modification can be based on the desired bodily function. For example, one or more parameters related to the intensity of the stimulation signal can be modulated. The modulation of the one or more pulse parameters of the stimulation signal related to intensity can recruit a different population of axons with each pulse. For example, the parameter related to intensity can be varied for each of the pulses. As another example, the pulse parameter related to intensity can be varied for a plurality of pulses according to the modulation pattern or modulation envelope (e.g., of any shape representing a time-varying alternation of one or more pulse parameters related to intensity of the stimulation signal). In some instances, a single parameter related to intensity can be modulated. In other instances, different parameters related to intensity can be modulated at different times. In still other instances, a plurality of different pulse parameters related to intensity can be modulated by the pulse generator 12 at the same time (or substantially the same time). The one or more stimulation parameters can be any parameter of a pulse and/or a pattern of pulses that relates to the intensity of the stimulation signal. Examples of stimulation parameters related to intensity can include amplitude, pulse width, interpulse interval, pulse shape, parameters affecting pulse shape, recharge phase amplitude, recharge delay, and the like.

At 66, the modulated stimulation signal can be applied (by activating one or more contacts of electrode 14) to the neural tissue of the individual to affect the bodily function. As noted, the electrode can be placed transcutaneously, subcutaneously, or directly on the neural tissue to be stimulated. In some instances, the neural tissue that the electrode can interface with can include a portion of the central nervous system (e.g., for deep brain stimulation, spinal stimulation, or the like). For example, deep brain stimulation can be used to treat movement disorders, such as essential tremor or Parkinson's disease. In another example, deep brain stimulation and/or spinal cord stimulation can also be used to manage pain. In other instances, the neural tissue that the electrode can interface with can include a portion of the peripheral nervous system (e.g., a nerve (e.g., an afferent nerve, an efferent nerve, and/or an autonomic nerve) and/or ganglia). For example, the bodily function can be a sensory function (e.g., perception), an autonomic function, a motor function, an organ function, and/or a cognitive function. In one example, the biological function can include sensory restoration in amputees. In another example, the biological function can include modulation of pain. In a further example, the biological function can include restoration of taste. In yet another example, the biological function can include regulation of swallowing. In still another example, the biological function can include regulation of gastric reflux. In yet another example, the biological function can include regulation of blood pressure, appetite, or the like. In still a further example, the biological function can include restoration of hearing, vision, or the like. In yet another example, the biological function can include restoration of sexual sensation or enhancement of sexual sensation. In a further example, the biological function can include genitourinary regulation, such as relieving incontinence, regulating voiding, and the like. In still another example, the biological function can include regulation of a movement disorder.

For the different biological functions, electrodes can be placed in different areas of the individual's body and the patterned intensity modulation of the stimulation signal can lead to recruitment of different populations of axons within the neural tissue. The electrodes can be placed transcutaneously, subcutaneously, or directly on the neural tissue to be stimulated. For example, in the case of nerve stimulation, the electrodes can be placed on the patient's skin (transcutaneous electrical nerve stimulation).

FIG. 7 shows an example of a method 70 method for modulating the intensity of a signal that can be used for the neural stimulation. At 72, a stimulation signal (e.g., SS) can be applied to neural tissue of an individual (e.g., by electrode 14). In some instances, the stimulation signal can be a time-varying electrical signal. For example, the stimulation signal can include a plurality of pulses. Each of the pulses can have the same shape and/or a different shape (e.g., rectangular, triangular, trapezoidal, sinusoidal, etc.). In some examples, the plurality of pulses can be charge-balanced (e.g., individually charge-balanced or a pattern of pulses can be charge-balanced). In other examples, the plurality of pulses can be applied for a short time, so that the plurality of pulses need not be charge-balanced.

At 74, a feedback signal (e.g., FS) can be received (e.g., by receiver 22) in response to the application of the feedback signal. For example, the feedback signal can include a user input, a feedback signal input from the neural tissue or other tissue, a sensor signal input, a time input, etc. The feedback signal can include, for example, an input related to a stimulation parameter and/or an input related to a stimulation paradigm defining a modulation pattern or envelope. In some instances, signal processing can be performed on the feedback signal (e.g., by receiver 22 and/or pulse generator 12). As an example, the signal processing can transform the input signal into data related to the input signal (e.g., PFS) that can be applied to modulate the stimulation signal.

At 76, an intensity parameter of the stimulation signal can be modulated based on the feedback signal (e.g., by pulse generator 12). In other instances, two or more intensity parameters of the stimulation signal can be modified based on the stimulation signal. The modulation of the one or more intensity parameters of the stimulation signal related to intensity can recruit a different population of axons with each pulse. For example, based on the feedback signal, the intensity parameter can be varied for each of the pulses. As another example, based on the feedback signal, the intensity parameter can be varied for a plurality of pulses according to a stimulation paradigm that defines a modulation pattern or modulation envelope (e.g., any time-varying shape, such as a sinusoid, a triangle, a trapezoid, or the like). In some instances, a single intensity parameter related to intensity can be modulated, while in other instances, different intensity parameters related to intensity can be modulated at different times and/or at the same time (or substantially the same time). Examples of intensity parameters that can be modulated include amplitude, pulse width, interpulse interval, pulse shape, parameters affecting pulse shape, recharge phase amplitude, recharge delay, and the like. Other examples of intensity parameters can include a parameter related to the modulation envelope (e.g., shape, frequency, amplitude, etc.).

FIG. 8 shows an example of a method 80 for affecting a desired bodily function with the neural stimulation. The neural stimulation can include patterned stimulation intensity (or "Ψ-stim") to recruit a population of axons to affect the desired bodily function. At 82, a stimulation signal (e.g., SS) with an intensity that is modulated with time (e.g., by pulse generator 12) can be applied to neural tissue of an individual (e.g., by electrode 14). For example, the intensity can be modulated with time based on a feedback signal. As noted, for example, the feedback signal can include a user input, a feedback signal input from the neural tissue or other tissue, a sensor signal input, a time input, etc. As noted, the neural stimulation can be applied to a normal individual, an amputee, a paralyzed individual, a diseased individual, or the like.

At 84, a different population of axons in the neural tissue can be recruited with each pulse of the stimulation signal. For example, the patterned stimulation intensity can be modulated with regard to timing and/or strength to alter an electric field delivered to the neural tissue from each pulse. At 88, a desired bodily function can be affected based on the recruited population of axons. For example, the bodily function can be a sensory function (e.g., perception), an autonomic function, a motor function, an organ function, and/or a cognitive function. In some instances, the patterned stimulation intensity can be specific to affect the desired bodily function.

V. Additional Devices, Systems, and Methods

Neural stimulation with patterned stimulation intensity (or "Ψ-stim") (e.g., according to the systems and methods discussed above) can be applied in the peripheral nervous system and/or the central nervous system of: a normal, able-bodied individual; an amputee; a paralyzed individual; or a diseased individual, such as an individual suffering from an autonomic, motor, and/or sensory deficit to affect a certain biological function. The patterned stimulation intensity allows the signal to mimic actual biological signals, allowing the biological functions to occur more naturally than other types of stimulation.

One example application of neural stimulation with patterned stimulation intensity can provide a "virtual" sensation to an individual. For instance, a median, ulnar and/or radial nerve can be stimulated to provide artificial sensation. In another example, the virtual sensation can enable a sensory-enabled (e.g., touch, sight, hearing, taste, smell, etc.) virtual reality, user interfaces (e.g., to computing devices), and telepresence.

In another example, the use of virtual sensation can include medical applications, such as a clinician performing a physical diagnosis of a patient from a remote location. Another example use of the virtual sensation can include virtual contact for gaming applications and/or to augment social media by allowing an individual to virtually contact another individual (e.g., to allow an individual to perceive the sensation of holding another individual's hand).

Another example can include use of an individual's fingers to enable perceived sensations that that the individual cannot otherwise physically or safely experience. With such a system, a carpenter can use his or her fingers to scan over a wall to feel a stud or wire instead of using conventional carpentry tools. In another example, an obstetrician can feel a fetus' heart beat while performing an in utero exam. In another example, ultrasound information indicating an irregular tissue mass in the breast, abdomen, or other bodily location can be "felt" by a clinician. Current sensing tools convert physical information to visual information that the user interprets. With patterned intensity modulation, a clinician may be able to better interpret and diagnose a patient using the sense of touch rather than, or in addition to, vision alone.

Another example use of virtual sensation can include robotic control, in which feedback from a robotics system (e.g., a drone pilot, a robotic aircraft, or the like) can be returned to an operator to improve control and operation of the robotics system by allowing the pilot can feel what is happening in or to the aircraft.

Other applications of the present disclosure may include situations where it is unsafe to actually (physically) experience a sensation. For example, a mechanic can diagnose engine performance by "feeling" vibrations or temperature information from sensors inside an engine. The pressures and forces within the engine would far exceed what could be safely felt, but the data from the sensors can be scaled and translated to touch sensations according to the present disclosure.

From the above description, those skilled in the art will perceive improvements, changes and modifications. Such improvements, changes and modifications are within the skill of one in the art and are intended to be covered by the appended claims.

What is claimed is:

1. A method comprising:
   receiving a signal in response to a device performing an action, wherein the device is at a location remote from a user, wherein the signal comprises a trigger for a virtual sensation, and wherein the virtual sensation connects one or more nerves of the user to the action of the device;
   configuring a stimulation signal with a pattern of stimulation intensities based on the trigger for the virtual sensation; and
   delivering the stimulation signal to one or more nerves to cause the virtual sensation.

2. The method of claim 1, wherein the one or more nerves comprise sensory fibers and/or autonomic fibers.

3. The method of claim 2, wherein the stimulation signal is configured to activate at least a portion of the sensory fibers and/or the autonomic fibers.

4. The method of claim 1, wherein the action is a mechanical action.

5. The method of claim 4, wherein the virtual sensation connects the one or more nerves to the mechanical action of the device in response to the mechanical action.

6. The method of claim 1, wherein the virtual sensation is translated and/or scaled from the signal.

7. The method of claim 6, wherein the signal is physiologically unsafe, but the virtual sensation is physiologically safe.

8. The method of claim 1, wherein the device is located in a healthcare setting.

9. The method of claim 8, wherein the virtual sensation enables a clinician to perform a procedure on a patient at a remote location.

10. The method of claim 8, wherein the virtual sensation enables a person to visit a patient at a remote location.

11. A system comprising:
    a pulse generator configured to:
       receive a signal in response to a device performing an action, wherein the device is at a location remote from a user, wherein the signal comprises a trigger for a virtual sensation; and
       configure a stimulation signal with a pattern of stimulation intensities based on the trigger for the virtual sensation; and
    at least one electrode configured to deliver the stimulation signal to one or more nerves of the user to cause the virtual sensation, wherein the virtual sensation connects the one or more nerves to the action of the device.

12. The system of claim 11, wherein the one or more electrodes comprise cuff electrodes configured to at least partially surround the one or more nerves.

13. The system of claim 11, wherein the action is a mechanical action.

14. The system of claim 11, wherein the device is located in a healthcare setting.

15. The system of claim 14, wherein the virtual sensation enables a clinician to perform a procedure on a patient at a remote location.

16. The system of claim 14, wherein the virtual sensation enables a person to visit a patient at a remote location.

17. The system of claim 11, wherein the stimulation signal is configured to activate at least a portion of sensory fibers and/or autonomic fibers within the one or more nerves.

18. The system of claim 11, wherein the signal is physiologically unsafe, but the virtual sensation is physiologically safe and translated and/or scaled from the signal.

* * * * *